(12) United States Patent
Tin

(10) Patent No.: US 8,591,504 B2
(45) Date of Patent: Nov. 26, 2013

(54) SYSTEMS AND METHODS FOR REGULATING PRESSURE LEVELS IN AN INTER-EXPANSION-ELEMENT SPACE OF A CRYOABLATION SYSTEM

(75) Inventor: Rebecca Tin, Mountain View, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 662 days.

(21) Appl. No.: 12/847,552

(22) Filed: Jul. 30, 2010

(65) Prior Publication Data

US 2011/0028960 A1 Feb. 3, 2011

Related U.S. Application Data

(60) Provisional application No. 61/230,245, filed on Jul. 31, 2009.

(51) Int. Cl.
*A61B 18/02* (2006.01)

(52) U.S. Cl.
USPC .......................................................... 606/21

(58) Field of Classification Search
USPC ............................................... 606/20–26, 34
See application file for complete search history.

(56) References Cited

U.S. PATENT DOCUMENTS

| | | | |
|---|---|---|---|
| 5,334,181 A * | 8/1994 | Rubinsky et al. | 606/22 |
| 5,800,488 A * | 9/1998 | Crockett | 607/105 |
| 6,283,959 B1 * | 9/2001 | Lalonde et al. | 606/21 |
| 6,383,180 B1 * | 5/2002 | Lalonde et al. | 606/22 |
| 7,273,479 B2 * | 9/2007 | Littrup et al. | 606/21 |
| 2006/0212026 A1 * | 9/2006 | Abboud et al. | 606/20 |

FOREIGN PATENT DOCUMENTS

| | | |
|---|---|---|
| WO | 03026719 A2 | 4/2003 |
| WO | 2006096272 A1 | 9/2006 |
| WO | 2006124177 A1 | 11/2006 |

* cited by examiner

*Primary Examiner* — Michael Peffley
*Assistant Examiner* — Daniel Fowler
(74) *Attorney, Agent, or Firm* — Seager, Tufte & Wickhem, LLC

(57) ABSTRACT

A cryoablation catheter assembly includes a catheter having a coolant outtake region and receives a guide tube and a coolant transfer tube. The coolant transfer tube receives and transfers coolant from a coolant source to an expansion element coupled to a distal portion of the catheter. The expansion element includes an outer layer disposed over an inner layer such that the expansion element defines an inter-expansion-element space between the inner layer and the outer layer and an intra-expansion-element space within the inner layer. The intra-expansion-element space is in fluid communication with the coolant outtake region and the coolant transfer tube. The inter-expansion-element space is in fluid communication with a fluid pathway that transfers fluids to a fluid-drawing source. A pressure regulation system is disposed along the fluid pathway and passively regulates the pressure in the inter-expansion-element space using at least one check valve.

18 Claims, 7 Drawing Sheets

SYSTEMS AND METHODS FOR REGULATING PRESSURE LEVELS IN AN INTER-EXPANSION-ELEMENT SPACE OF A CRYOABLATION SYSTEM

CROSS-REFERENCE TO RELATED APPLICATIONS

This application claims the benefit of U.S. Provisional Application No. 61/230,245, filed Jul. 31, 2009, the entire disclosure of which is incorporated herein by reference.

TECHNICAL FIELD

The present invention is directed to the area of cryoablation systems and methods of making and using the systems. The present invention is also directed to cryoablation systems with pressure regulation systems for regulating pressure within an inter-expansion-element space of a cryoablation system, as well as systems and methods of making and using the pressure regulation systems, expansion elements, and cryoablation systems.

BACKGROUND

Cryoablation systems have been used to reduce, or even eliminate, undesired electrical activity between adjacent cardiac tissues of the heart (arrhythmias). One common type of arrhythmia, atrial fibrillation, is a result of abnormal electrical signals interfering with the normal electrical signal propagation along the tissues of the heart.

Atrial fibrillation often originates near the ostia of the pulmonary veins. Cryoablation systems can be used to form lesions on patient tissue in proximity to the ostia, where the pulmonary veins open into the left atrium of the heart. The cold-induced lesions can effectively block the initiation or propagation of the abnormal electrical signals, thereby preventing the abnormal electrical signals from interfering with the normal electrical signal propagation along the tissues of the heart.

BRIEF SUMMARY

In one embodiment, a cryoablation catheter assembly may include a catheter, a guide tube, a coolant transfer tube, an expansion element, and a pressure regulation system. The catheter has a distal portion, a proximal portion, and a longitudinal length. The catheter is configured and arranged for insertion into patient vasculature. The catheter may include a body and defines at least one coolant outtake region extending along at least a portion of the catheter. The guide tube may be at least partially disposed in the catheter. The coolant transfer tube may be at least partially disposed in the catheter and configured and arranged to receive and transfer coolant from a coolant source to a distal end of the coolant transfer tube. The expansion element may be coupled to the distal portion of the body of the catheter. The expansion element may include an outer layer disposed over an inner layer such that the expansion element defines an inter-expansion-element space between the inner layer and the outer layer and an intra-expansion-element space within the inner layer. The intra-expansion-element space can be in fluid communication with the at least one coolant outtake region and the distal end of the coolant transfer tube. The inter-expansion-element space may be in fluid communication with a fluid pathway. The fluid pathway is configured and arranged to transfer fluids from the inter-expansion-element space to a fluid-drawing source. The pressure regulation system is disposed along the fluid pathway and is configured and arranged to passively regulate the pressure in the inter-expansion-element space using at least one check valve.

In another embodiment, a cryoablation system may include a catheter, a guide tube, a coolant transfer tube, an expansion element, a pressure regulation system, a coolant source, a fluid-drawing source, and a control module. The catheter has a distal portion, a proximal portion, and a longitudinal length. The catheter is configured and arranged for insertion into patient vasculature. The catheter may include a body and define at least one coolant outtake region extending along at least a portion of the catheter. The guide tube may be at least partially disposed in the catheter. The coolant transfer tube may be at least partially disposed in the catheter and configured and arranged to receive and transfer coolant from a coolant source to a distal end of the coolant transfer tube. The expansion element may be coupled to the distal portion of the body of the catheter. The expansion element may include an outer layer disposed over an inner layer such that the expansion element defines an inter-expansion-element space between the inner layer and the outer layer and an intra-expansion-element space within the inner layer. The intra-expansion-element space can be in fluid communication with the at least one coolant outtake region and the distal end of the coolant transfer tube. The inter-expansion-element space can be in fluid communication with a fluid pathway. The fluid pathway is configured and arranged to transfer fluids from the inter-expansion-element space to a fluid-drawing source. The pressure regulation system may be disposed along the fluid pathway and is configured and arranged to passively regulate the pressure in the inter-expansion-element space using at least one check valve. The coolant source couples to the coolant transfer tube. The fluid-drawing source couples to the at least one coolant outtake region and to the fluid pathway. The control module couples to the catheter, the coolant source, and the fluid-drawing source. The control module may include a coolant flow controller that is configured and arranged for controlling the flow of coolant along the coolant transfer tube and the at least one coolant outtake region.

In yet another embodiment, a method for cryoablating patient tissue may include inserting a catheter in patient vasculature. The catheter has a distal portion and defines at least one coolant outtake region. The catheter may be guided in proximity to patient tissue to be ablated. Coolant may be drawn from a coolant source such that coolant flows along a coolant transfer tube disposed in the catheter and is sprayed into an expansion element that is disposed at the distal portion of the catheter, thereby expanding the expansion element and reducing the temperature of the expansion element to a temperature sufficiently low enough to ablate patient tissue upon contact. The expansion element may include an inner layer and an outer layer disposed over the inner layer. The coolant may be sprayed into an intra-expansion-element space within the inner layer. The expansion element defines an inter-expansion-element space between the inner layer and the outer layer. Patient tissue is contacted with the expanded expansion element for a time period adequate to ablate tissue contacting the expansion element. The expansion element is deflated by drawing the coolant from the intra-expansion-element space along the at least one coolant outtake region and also drawing fluid from the inter-expansion-element space along a fluid pathway. The coolant and the fluid are drawn by a fluid-drawing source. The pressure is passively regulated within the inter-expansion-element space using at least one check valve positioned along the fluid pathway.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of cryoablation systems and methods of making and using the systems. The present invention is also directed to cryoablation systems with pressure regulation systems for regulating pressure within an inter-expansion-element space of a cryoablation system, as well as systems and methods of making and using the pressure regulation systems, expansion elements, and cryoablation systems.

A cryoablation system can include a catheter configured and arranged for transporting coolant to and from a target location within a patient, an expansion element disposed at a distal portion of the catheter for ablating contacted patient tissue, a coolant source coupled to the catheter for supplying the coolant, and a control module for controlling or monitoring one or more of the operations of the system (e.g., controlling coolant flow, monitoring catheter pressure or temperature, or the like). The expansion element can be positioned at a target location in patient vasculature (e.g., the left atrium of the heart) and the coolant can be input to the catheter and directed to the expansion element. When the coolant contacts the expansion element, the coolant absorbs heat and expands, thereby causing the expansion element to expand and reduce in temperature to a level low enough to ablate patient tissue upon contact. The coolant flows out of the expansion element and back to a proximal end of the catheter. As the coolant flows out of the expansion element, the expansion element deflates and the catheter may be removed from the patient vasculature.

Figure 1:
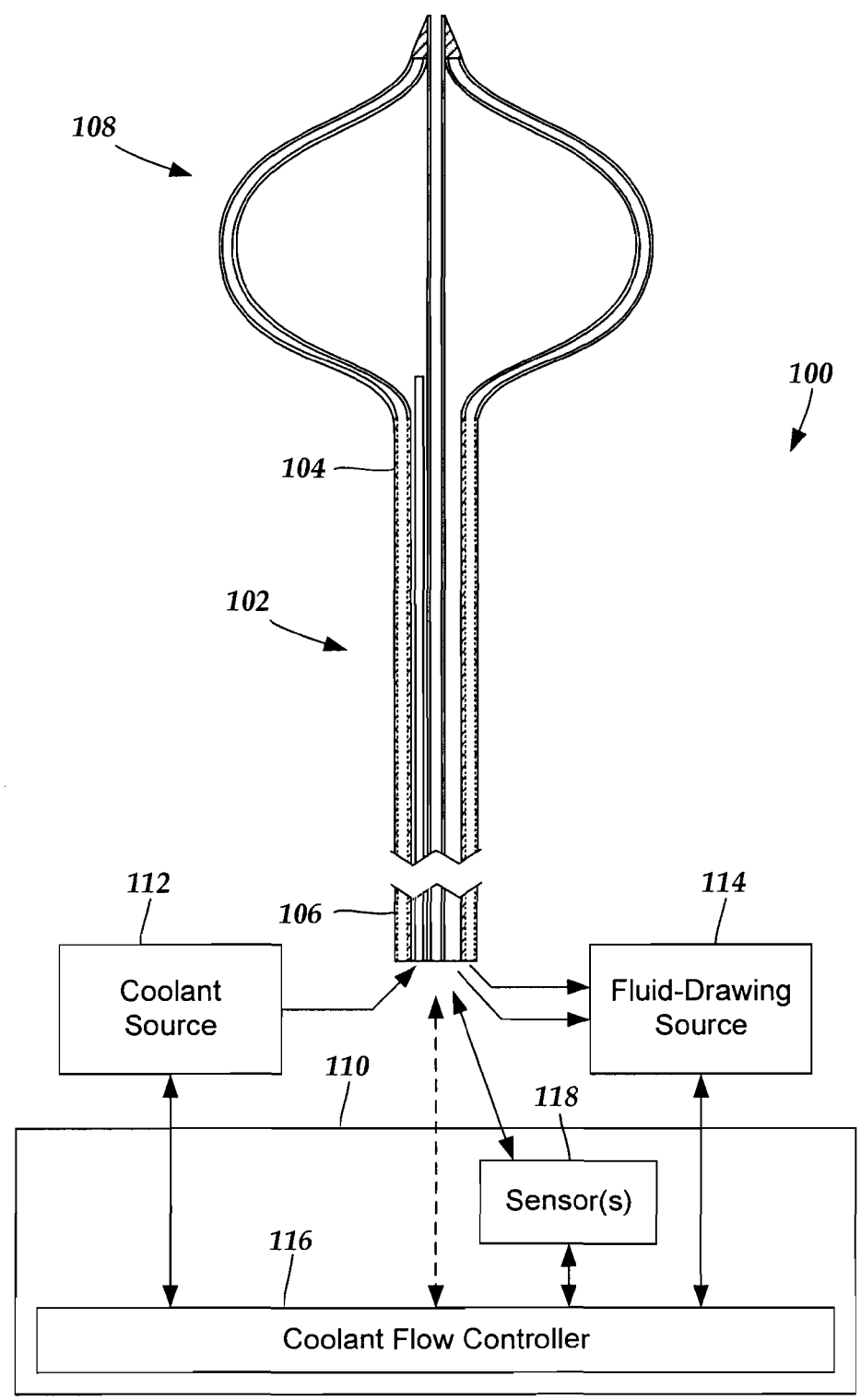
FIG. 1 is a schematic partial cross-sectional and partial block diagram view of one embodiment of a cryoablation system, according to the invention.

FIG. 1 illustrates schematically one embodiment of a cryoablation system 100. The cryoablation system 100 includes a catheter 102 with a distal portion 104 and a proximal portion 106. An expansion element 108 is coupled to the distal portion 104 of the catheter 102. A control module 110, a coolant source 112, and a fluid-drawing source 114 (e.g., a vacuum source, a pump, or the like) are each coupled to the proximal portion 106 of the catheter 102. The control module 110 includes a coolant flow controller 116 to control the flow of coolant within the catheter 102 to and from the expansion element 108. In at least some embodiments, the control module 110 also includes one or more sensors 118 for monitoring one or more' conditions (e.g., pressure, temperature, or the like) within the catheter 102.

In at least some embodiments, the coolant source 112 includes a coolant under pressure. A variety of different coolants may be used to provide a low enough temperature to ablate tissue upon contact. In preferred embodiments, the coolant is a low freezing point liquid with a low vaporization temperature which may be input to the catheter 102 as a liquid that is sprayed into the expansion element 108, where the liquid coolant absorbs heat and is vaporized or atomized. Examples of suitable liquids include, but are not limited to, a liquefied gas (e.g., nitrogen, nitrous oxide, carbon dioxide, or the like), one or more chlorofluorocarbons, one or more hydrochlorofluorocarbons, ethanol mixtures, saline solutions, or the like. It will be understood that a combination of one or more coolants may be used in the cryoablation system 100.

Figure 2A:
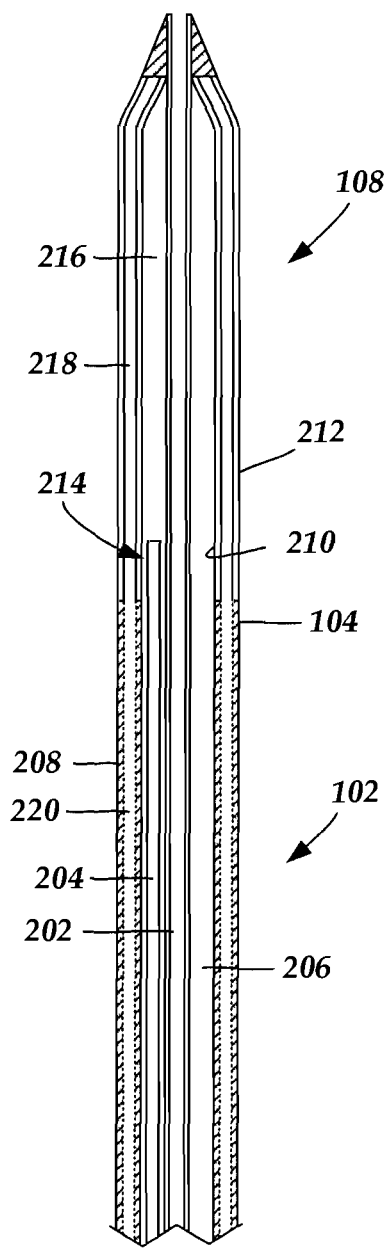
FIG. 2A is a schematic longitudinal cross-sectional view of one embodiment of an expansion element coupled to a distal portion of a catheter of the cryoablation system of FIG. 1, the expansion element in a deflated configuration, according to the invention.

During a typical cryoablation procedure, the distal portion 104 of the catheter 102 is inserted into patient vasculature for delivery of the expansion element 108 to one or more ablation sites. FIG. 2A is a schematic longitudinal cross-sectional view of one embodiment of the distal portion 104 of the catheter 102 and the expansion element 108. In FIG. 2A, the expansion element 210 is shown in a deflated configuration. A guide tube 202, a coolant transfer lumen 204, and at least one coolant outtake region 206 are each disposed in a flexible body 208 of the catheter 102.

In at least some embodiments, the expansion element 108 includes an inner layer 210 and an outer layer 212 disposed over the inner layer 210. FIGS. 1-3, and 5 show the expansion element 108 having two layers. It will be understood that the expansion element 108 may, instead, have more than two layers.

The expansion element 108 may be formed from any elastic or semi-elastic material, such as one or more thermoplastics (e.g., polyether block amide, or the like), or other plastics (e.g., nylon, urethane, or the like) that maintain elasticity over a wide range of temperatures, particularly at the temperature of the expanded coolant. In at least some embodiments, the expansion element 108 is semi-elastic, wherein the size of the expansion element 108 does not change in response to incremental changes in pressure that are below 5 psi (about 34.5× $10^3$ Pa).

The guide tube 202 may be formed from any flexible material (e.g., a thermoplastic, or the like) that maintains elasticity over a wide range of temperatures, particularly at the temperature of the expanded coolant. The guide tube 202 is optionally configured and arranged to receive a stiffening member (e.g., a stylet, or the like) to facilitate guiding of the catheter 102 to a target location within patient vasculature by providing additional rigidity to the catheter 102. In at least some embodiments, the guide tube 202 defines a lumen through which the stiffening member can be extended. In at least some embodiments, the guide tube extends along a longitudinal length of the catheter 102 from the proximal portion (106 in FIG. 1) of the catheter 102 to a position that is beyond the distal portion 104 of the catheter 102.

The coolant transfer tube 204 extends along the longitudinal length of the catheter 102 from the proximal portion (106 in FIG. 1) of the catheter 102. The coolant transfer tube 204 defines a lumen. A proximal end of the lumen is coupled to the coolant source (112 in FIG. 1). The coolant transfer tube 204 includes a distal end 214 that opens into the expansion element 108.

The coolant outtake region 206 is configured and arranged to accommodate coolant exiting the expansion element 108. The coolant outtake region 206 extends along the longitudinal length of the catheter 102 from the proximal portion (106 in FIG. 1) of the catheter 102 to the expansion element 108. In some embodiments, the coolant outtake region 206 includes one or more tubes that define one or more lumens. In other embodiments, the coolant outtake region 206 includes one or more open regions within the body 208 of the catheter 102 and exterior to the guide tube 202 and the coolant transfer tube 204.

In at least some embodiments, a proximal end of the expansion element 108 couples to the distal portion 104 of the catheter 102. In at least some embodiments, the distal end of the expansion element 108 is coupled to the guide tube 202. In at least some embodiments, the expansion element 108 defines an intra-expansion-element space 216 within the inner layer 210. In at least some embodiments, the intra-expansion-element space 216 is in fluid communication with the distal end 214 of the coolant transfer tube 204. In at least some embodiments, the intra-expansion-element space 216 is in fluid communication with the at least one coolant outtake region 206. In at least some embodiments, the distal end 214 of the coolant transfer tube 204 extends beyond the distal portion of the catheter 102 and into the intra-expansion-element space 216. In at least some embodiments, the intra-expansion-element space 216 is in fluid communication with the fluid-drawing source (114 in FIG. 1) via a proximal end of the coolant outtake region 206.

In at least some embodiments, a vacuum is maintained in a space between the inner layer 210 and the outer layer 212 (i.e., in an inter-expansion-element space 218) of the expansion element 108. In at least some embodiments, the inter-expansion-element space 218 is also in fluid communication with the fluid-drawing source 114 via a fluid pathway 220. In FIG. 2A, the fluid pathway 220 is shown as a space within the body 208 of the catheter 102. In at least some embodiments, the fluid pathway 220 extends beyond the catheter 102 (see e.g., FIGS. 4A-4B). In at least some embodiments, the fluid pathway 220 extends into a handle (see e.g., 402 in FIGS. 4A-4B) configured and arranged to couple to the proximal end 106 of the catheter 102. In at least some embodiments, the fluid pathway 220 extends to the fluid-drawing source (114 in FIG. 1). In at least some embodiments, the fluid pathway 220 is in fluid communication with the coolant outtake region 206. In at least some embodiments, the fluid pathway 220 is in fluid communication with ambient air external to the catheter 102. In at least some embodiments, the fluid pathway 220 is in fluid communication with ambient air external to a patient when the distal end 104 of the catheter 102 is inserted into the patient. In at least some embodiments, the fluid pathway 220 is in fluid communication with ambient air external to the cryoablation system 100.

The distal end 214 of the coolant transfer tube 204 is configured and arranged to output coolant from the coolant transfer tube 204 to the intra-expansion-element space 216. In at least some embodiments, the distal end 214 of the coolant transfer tube 204 is open. In at least some embodiments, the distal end 214 of the coolant transfer tube 204 defines one or more spray apertures. In at least some embodiments, the coolant is output as a sprayed liquid that vaporizes or atomizes as the liquid is output from the distal end 214 of the coolant transfer tube 204. In at least some embodiments, when the coolant enters the intra-expansion-element space 216, the expansion element 108 absorbs heat and expands, thereby reducing the temperature of the expansion element 108 to a temperature sufficiently low enough to ablate patient tissue upon contact.

The reduction in temperature of the expansion element 108 may be due to one or more of the Joule-Thompson effect or the latent heat of vaporization. The Joule-Thompson effect describes the cooling effect that comes about when a compressed non-ideal gas expands into a region of low pressure (e.g., within the expansion element 108). The latent heat of vaporization describes heat being released as a result of the phase change from a liquid to a gas (e.g., the liquefied coolant vaporizing upon entering the expansion element 108).

Figure 2B:
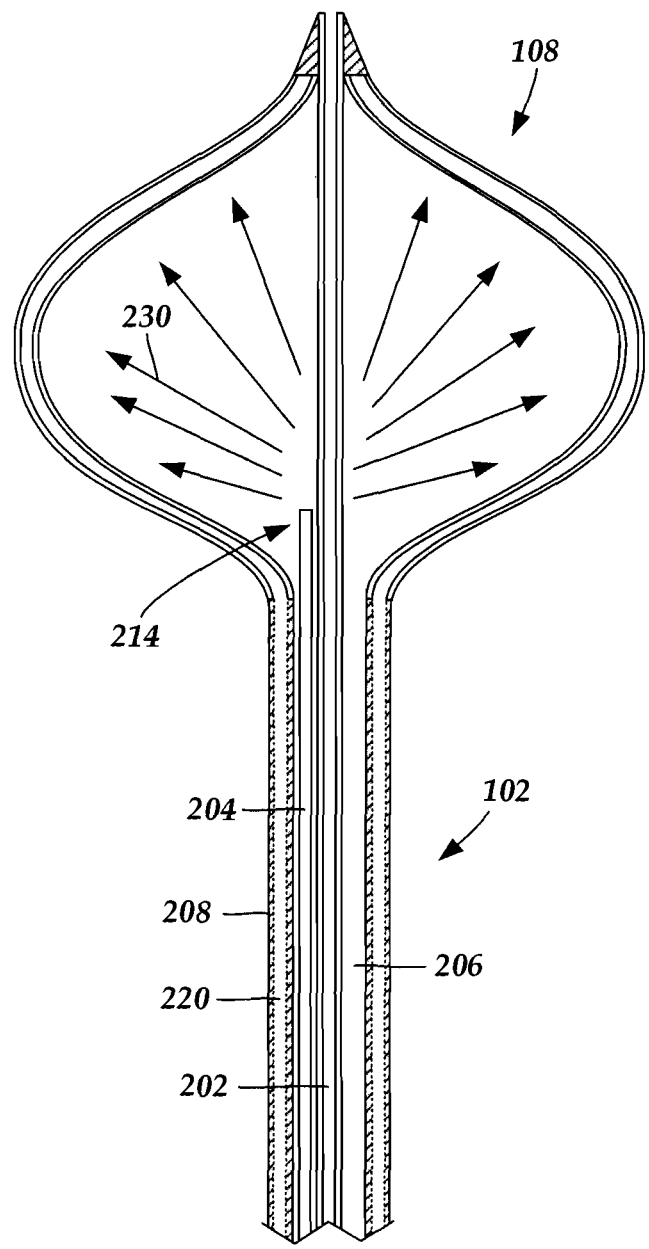
FIG. 2B is a schematic longitudinal cross-sectional view of one embodiment of an expansion element coupled to a distal portion of a catheter of the cryoablation system of FIG. 1, the expansion element an inflated configuration, according to the invention.

FIG. 2B is a schematic longitudinal cross-sectional view of one embodiment of the expansion element 108 in an inflated configuration. Directional arrows, such as arrow 230, show the flow of coolant from the distal end 214 of the coolant transfer tube 204 to the intra-expansion-element space 216. The expanded gas dissipates down the catheter 102 along the coolant outtake region 206. In at least some embodiments, the fluid-drawing source (114 in FIG. 1) is used to draw the expanded, heated, and gaseous coolant along the coolant outtake region 206 from the expansion element 108 out the proximal end of the coolant outtake region 206. In at least some embodiments, the fluid-drawing source 114 is also used to maintain a vacuum in the inter-expansion-element space 218. In at least some embodiments, the fluid-drawing source 114 maintains a vacuum in the inter-expansion-element space 218 via the fluid pathway 220.

Typically, the catheter 102 is inserted in patient vasculature and guided to an ablation site, such as the ostia of the pulmonary veins in the left atrium of the heart of the patient. In at least some embodiments, the expansion element 108 is maintained in a vacuum during insertion. Sometime after the expansion element is in proximity to the ablation site, coolant from the coolant source (112 in FIG. 1) is released into the catheter 102. In at least some embodiments, the coolant source 112 includes a pressurized container or pump. In at least some embodiments, the lower pressure in the expansion element 108 draws the coolant along the coolant transfer tube 204 and into the expansion element 108. In at least some embodiments, the fluid-drawing source (114 in FIG. 1) may be used to control the rate of flow of the coolant within the catheter 102. The rate of flow of the coolant within the catheter 102 may be adjusted to a rate appropriate to the specific type of operation.

In some embodiments, a cryoablation procedure involves ablating patient tissue at multiple ablation sites. When multiple tissue ablations are performed, the expansion element 108 may be deflated between one or more of the tissue ablations and moved to the next ablation site. In at least some embodiments, the expansion element 108 is deflated between one or more of the tissue ablations to an ambient pressure. Deflation of the expansion element 108 after a tissue ablation may result in the expansion element 108 forming an unpredictable shape. Some shapes may make movement of the catheter 102 (or retraction of the expansion element 108 after completion of each ablation) difficult to achieve. Thus, it would be advantageous for the expansion element to deflate to a predictable shape that facilitates subsequent movement or retraction of the expansion element 108.

As discussed above, in at least some embodiments, both the intra-expansion-element space 216 and the inter-expansion-element space 218 are in fluid communication with the fluid-drawing source 114. As also discussed above, the fluid-drawing source 114 may be used to control the rate of flow of the coolant within the catheter 102. In at least some embodiments, the fluid-drawing source 114 is used during an entire cryoablation procedure to draw fluid from both the intra-expansion-element space 216 and the inter-expansion-element space 218. It may be the case that the rate of fluid withdrawal used to effectively exhaust the intra-expansion-element space 216 may form pressure levels within the inter-expansion-element space 218 that are undesirable, or even unsafe. For example, a rate of fluid withdrawal used to effectively exhaust the intra-expansion-element space 216 may produce excessively low pressure in the inter-expansion-element space 218 which may cause the expansion element 108 to form unpredictable shapes. Some of the shapes formed may render the catheter 102 immobile, or obstruct refraction of the expansion element 108. Thus, it may be desirable to use different rates of fluid withdrawal for each of the intra-expansion-element space 216 and the inter-expansion-element space 218.

Figure 3:
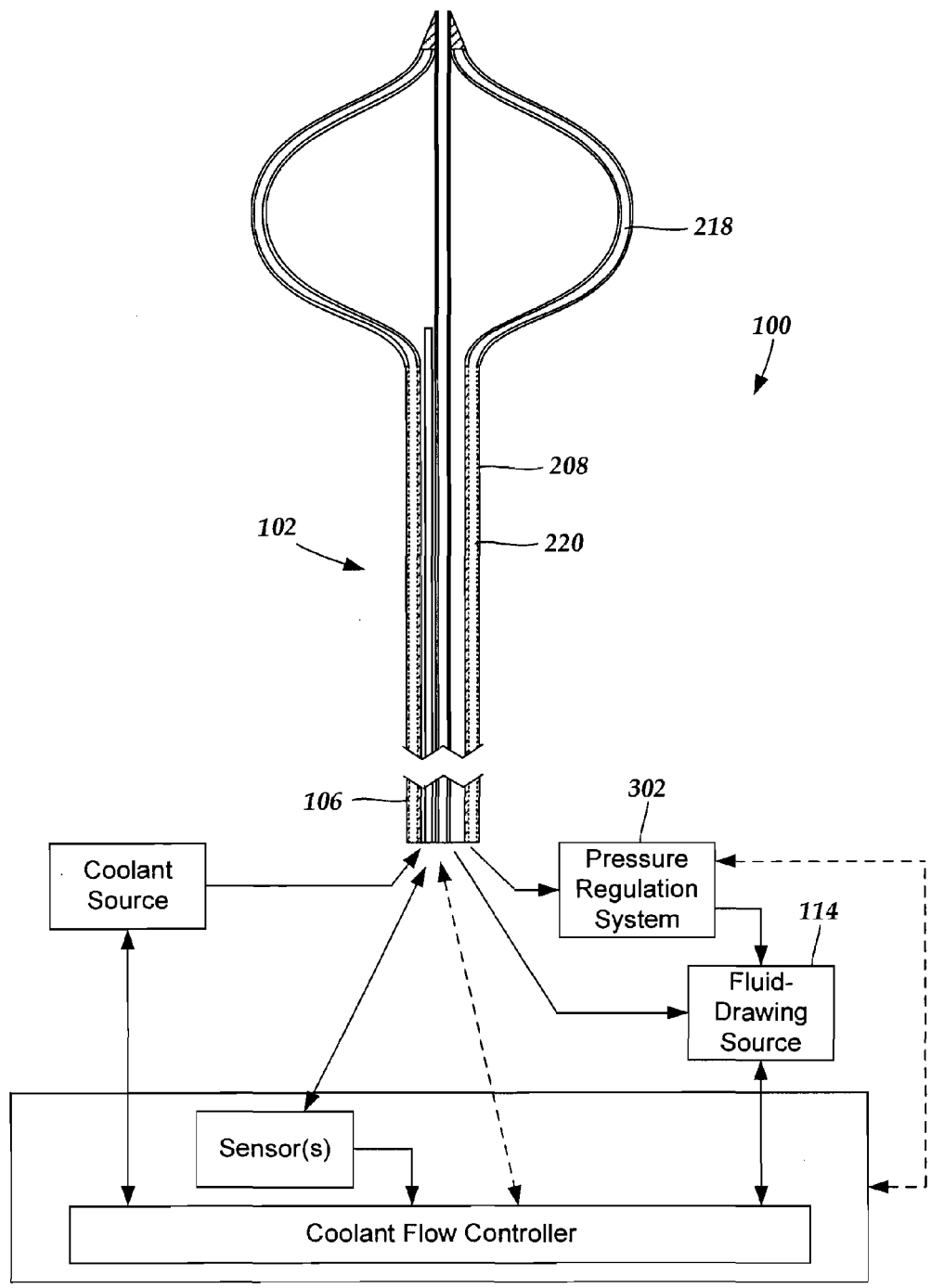
FIG. 3 is a schematic partial cross-sectional and partial block diagram view of another embodiment of a cryoablation system, the cryoablation system including a pressure regulation system for regulating the pressure within an inter-expansion-element space, according to the invention.

In at least some embodiments, the cryoablation system includes a pressure regulation system for regulating pressure within the inter-expansion-element space 218. FIG. 3 is a schematic partial cross-sectional and partial block diagram view of another embodiment of the cryoablation system 100. The cryoablation system 100 includes a pressure regulation system 302 along the fluid pathway 220 between the inter-expansion-element space 218 and the fluid-drawing source 114. In FIG. 3, and in subsequent figures, the fluid pathway 220 is shown extending from the inter-expansion-element space 218 to the fluid-drawing source 114.

In at least some embodiments, the pressure regulation system 302 is passive (i.e., the pressure regulation system 302 does not use pumps to regulate pressure). In at least some embodiments, the pressure regulation system 302 uses one or more check valves to passively regulate the pressure within the inter-expansion-element space 218 relative to another location. In at least some embodiments, the pressure within the intra-expansion-element space 218 is regulated relative to either ambient pressure or the level of pressure in a region adjacent to the fluid-drawing source (114 in FIG. 1).

A check valve is a self-actuated mechanical device that allows fluid flow from a region of relatively high pressure to a region of relatively low pressure when the pressure differential between the two regions meets or exceeds a particular threshold value. When the pressure differential between the two regions meets or exceeds a threshold value, the check valve opens and bulk fluid movement occurs from the relatively high-pressure region to the relatively low-pressure region until the pressures equalize between the two regions. Typically, once the pressure differential between the relatively-high region and the relatively-low region fall below the threshold pressure differential, the check valve closes until the pressure differential between the two regions once again meets or exceeds the threshold pressure differential of the check valve.

Check valves can be formed to have different pressure threshold values. Check valves may be formed from any suitable biocompatible material if the check valve is intended to be inserted into the patient. Check valves may include many different designs suitable for opening when a predetermined pressure differential is met or exceeded. For example, a check valve may include one or more movable components (e.g., diaphragms, balls, duckbills, hinged gates, rotatable gates, or the like or combinations thereof) configured and arranged to move or change shape, size, or orientation to form an opening between two regions when a predetermined pressure differential is met or exceeded.

Figure 4A:
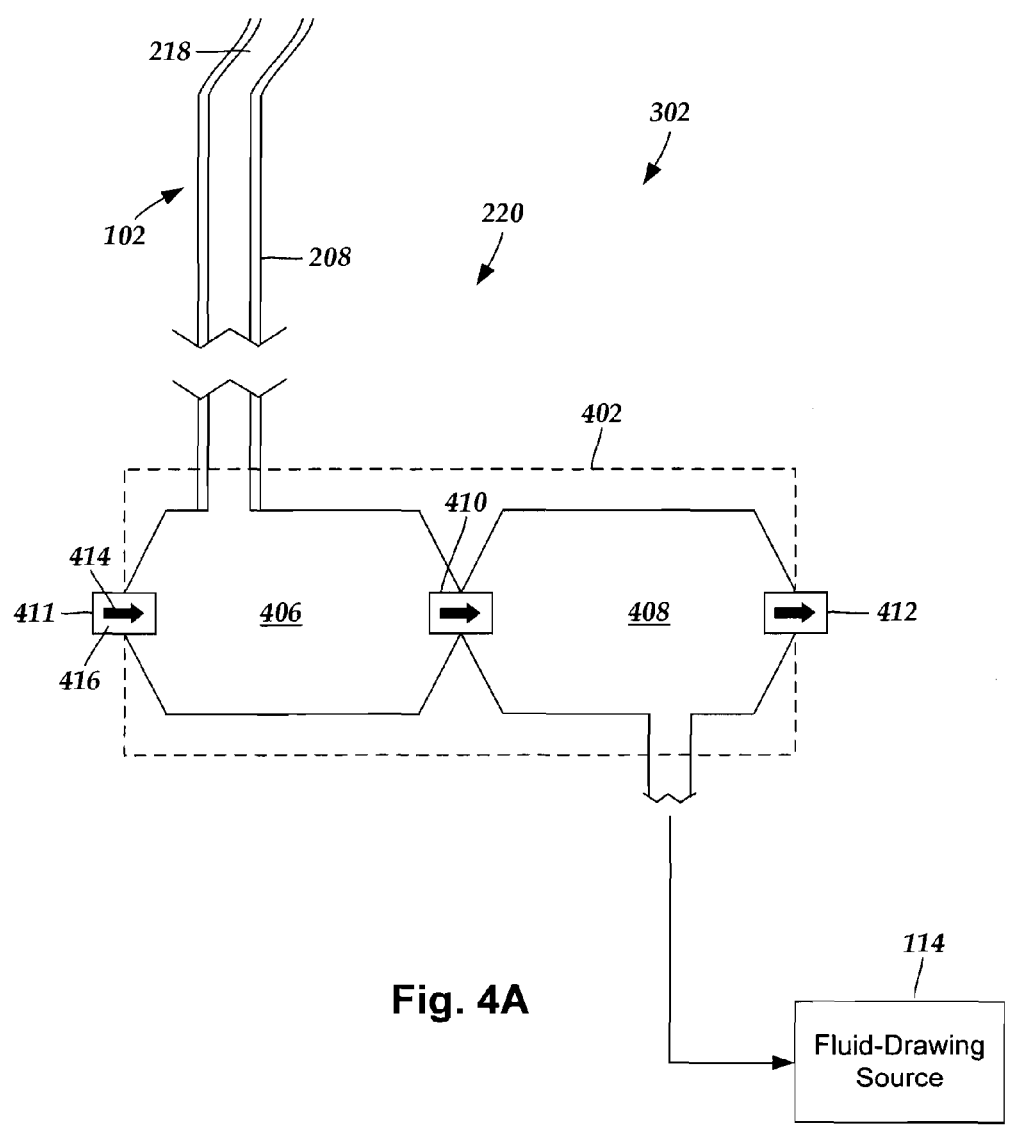
FIG. 4A is a schematic representation of one embodiment of the pressure regulation system of FIG. 3, the pressure regulation system regulating the pressure of the inter-expansion-element space relative to a pressure offset of ambient pressure and relative to a pressure offset to the fluid-drawing source, according to the invention.

FIG. 4A is a schematic representation of one embodiment of the fluid pathway 220 between the inter-expansion-element space 218 and the fluid-drawing source 114. In FIG. 4A the pressure within the inter-expansion-element space 218 is regulated by comparing the pressure within the inter-expansion-element space 218 to a region external to the catheter 102 ("ambient pressure"). In FIG. 4A, the fluid pathway 220 is shown partially defined along the body 208 of the catheter 102, partially defined within a handle 402 coupled to the catheter 102, and partially extending from the handle 402 to the fluid-drawing source 114. In alternate embodiments, the fluid pathway 220 does not extend into the handle 402. In at least some embodiments, the fluid pathway 220 extends directly from the catheter 102 to the fluid-drawing source 114.

In at least some embodiments, the fluid pathway 220 is divided into two regions 406 and 408 that are separated from one another by a check valve 410. The region 406 includes the inter-expansion-element space 218 and the region 408 includes the fluid-drawing source 114. The region 406 additionally includes a check valve 411 that separates the region 406 from ambient pressure. The check valves 410 and 411 are each shown as an arrow in a box, such as arrow 414 in box 416. The direction of the arrow shows the expected direction of bulk fluid movement when the check valve is opened. In other words, when the check valve is opened, the arrow points from a relatively high-pressure region to a relatively low-pressure region.

The check valves 410 and 411 can be positioned anywhere along the fluid pathway 220. In FIG. 4A, the check valves 410 and 411 are shown schematically positioned in the handle 402. In at least some embodiments, at least one of the check valves 410 and 411 is positioned along the body 208 of the catheter 102. In at least some embodiments, at least one of the check valves 410 and 411 is positioned external to the catheter 102 and the handle 402.

The check valve 410 is positioned somewhere along the fluid pathway 220 such that the check valve 410 forms a gate between the regions 406 and 408. The check valve 410 regulates the fluid flow between region 406 (which includes the inter-expansion-element space 218) and the region 408 (which includes the fluid-drawing source 114). As discussed above, the check valve 410 can be formed such that the check valve 410 opens when a desired threshold pressure differential is reached on opposing sides of the check valve 410.

Under operating conditions, the check valve 410 opens when the pressure within the region 406 is at a level that is at least a threshold pressure differential of the check valve 410 above the pressure level within the region 408. When the check valve 410 opens, bulk fluid movement occurs from the region 406 to the region 408 until the pressure differential between the regions 406 and 408 drops to a level that is below the threshold pressure differential of the check valve 410 and, accordingly, the check valve 410 closes.

For example, in at least some embodiments, the check valve 410 can be formed to open when the pressure in the region 406 is at least three pounds per square inch (about $2 \times 10^4$ Pa) greater than the pressure in the region 408. In at least some embodiments, the check valve 410 can be formed to open when the pressure in the region 406 is at least four pounds per square inch (about $3 \times 10^4$ Pa) greater than the pressure in the region 408.

In at least some embodiments, the check valve 410 can be formed to open when the pressure in the region 406 is at least five pounds per square inch (about $3.5 \times 10^4$ Pa) greater than the pressure in the region 408. In at least some embodiments, the check valve 410 can be formed to open when the pressure in the region 406 is at least six pounds per square inch (about $4 \times 10^4$ Pa) greater than the pressure in the region 408. In at least some embodiments, the check valve 410 can be formed to open when the pressure in the region 406 is at least seven pounds per square inch (about $5 \times 10^4$ Pa) greater than the pressure in the region 408.

The check valve 411 can be positioned anywhere within the region 406 such that the check valve 411 opens to the outside environment external to the catheter 102. Under operating conditions, the check valve 411 opens when the pressure of the inter-expansion-element space 218 is at least a threshold differential of the check valve 411 below ambient pressure. Accordingly, when the check valve 411 opens, bulk fluid movement occurs from the outside environment to the region 406 until the pressure differential between the region 406 and ambient pressure drops to a level below the threshold pressure differential of the check valve 411 and the check valve 411 closes.

In other words, when the pressure of the inter-expansion-element space 218 rises to a level above a pressure within the region 408 that meets or exceeds the threshold pressure differential of the check valve 410, the check valve 410 opens and bulk fluid movement occurs from the region 406 to the region 408, thereby lowering the pressure in the region 406. Similarly, when the pressure of the inter-expansion-element space 218 lowers to a level below ambient pressure that meets or exceeds the threshold pressure differential of the check valve 411, the check valve 411 opens and bulk fluid movement occurs from the outside environment into the region 406, thereby increasing the pressure of the region 406.

In at least some embodiments, the check valve 411 is set to open at a pressure differential that is no lower than the pressure differential that causes the check valve 410 to open. For example, in at least some embodiments, the check valve 411 can be set to open when the pressure in the region 406 is at least three pounds per square inch (about $2 \times 10^4$ Pa) less than ambient pressure. In at least some embodiments, the check valve 411 can be set to open when the pressure in the region 406 is at least five pounds per square inch (about $3.5 \times 10^4$ Pa) less than ambient pressure. In at least some embodiments, the check valve 411 can be set to open when the pressure in the region 406 is at least seven pounds per square inch (about $5 \times 10^4$ Pa) less than ambient pressure. In at least some embodiments, the check valve 411 can be set to open when the pressure in the region 406 is at least nine pounds per square inch (about $6 \times 10^4$ Pa) less than ambient pressure. In at least some embodiments, the check valve 411 can be set to open when the pressure in the region 406 is at least ten pounds per square inch (about $7 \times 10^4$ Pa) less than ambient pressure. In at least some embodiments, the check valve 411 is set to open at a pressure differential that is equal to or greater than the pressure differential that causes the check valve 410 to open.

It is possible that the fluid pathway 220 may become over-pressurized during operation due to one or more obstructions. In at least some embodiments, the pressure regulation system 402 also includes a pressure relief check valve 412 for reducing pressure levels that are significantly higher than pressures obtained during normal operating conditions. The pressure relief check valve 412 may be positioned anywhere along the fluid pathway 220. In at least some embodiments, the pressure relief check valve 412 is positioned in the region 408. In at least some embodiments, the pressure relief check valve 412 opens into the outside environment. In at least some embodiments, the pressure relief check valve 412 opens into a region external to the handle 402. In at least some embodiments, the pressure relief check valve 412 opens into a region external to the catheter 102. In at least some embodiments, the pressure relief check valve 412 opens into the control module (110 in FIG. 1).

The pressure relief check valve 412 has a threshold pressure differential that is higher than the check valves 410 and 411. In at least some embodiments, the pressure relief check valve 412 does not open when the cryoablation system is operating under normal conditions. In at least some embodiments, the pressure relief check valve 412 opens when the pressure in the fluid pathway 220 is at a level that is considered to be unsafe because the pressure is significantly greater than ambient pressure (i.e., a critical pressure level). Accordingly, when the pressure relief check valve 412 opens, bulk movement of fluid occurs through the pressure relief check valve 412 from the fluid pathway 220 to a region external to the cryoablation system, reducing the pressure within the fluid pathway 220.

For example, in at least some embodiments, the pressure relief check valve 412 can be set to open when the pressure within the fluid pathway 220 is at least 5 pounds per square inch (about $10 \times 10^4$ Pa) greater than ambient pressure. In at least some embodiments, the pressure relief check valve 412 can be set to open when the pressure within the fluid pathway 220 is at least 10 pounds per square inch (about $14 \times 10^4$ Pa) greater than ambient pressure. In at least some embodiments, the pressure relief check valve 412 can be set to open when the pressure within the fluid pathway 220 is at least 15 pounds per square inch (about $14 \times 10^4$ Pa) greater than ambient pressure. In at least some embodiments, the pressure relief check valve 412 can be set to open when the pressure within the fluid pathway 220 is at least 20 pounds per square inch (about $14 \times 10^4$ Pa) greater than ambient pressure. In at least some embodiments, the pressure relief check valve 412 can be set to open when the pressure within the fluid pathway 220 is at least 25 pounds per square inch (about $17 \times 10^4$ Pa) greater than ambient pressure. In at least some embodiments, the pressure relief check valve 412 can be set to open when the pressure within the fluid pathway 220 is at least 30 pounds per square inch (about $20.5 \times 10^4$ Pa) greater than ambient pressure. In at least some embodiments, the pressure relief check valve 412 can be set to open when the pressure within the fluid pathway 220 is at least 35 pounds per square inch (about $24 \times 10^4$ Pa) greater than ambient pressure.

It will be understood that additional check valves can be incorporated into the fluid pathway 220 to perform the same functions of the check valves 410-412. Additionally, the diameters of the openings of the check valves 410-412 through which fluids flow when the check valves 410-412 are open can be adjusted to control the flow rates of fluids through open check valves 410-412. For example, in at least some embodiments, the check valve 410 includes an opening with a diameter that is small enough to reduce the work load of the fluid-drawing source 114. As another example, in at least some embodiments, the opening of the pressure relief check valve 412 has a diameter that is sufficiently large to allow fluid to quickly move out of the fluid pathway 220.

Figure 4B:
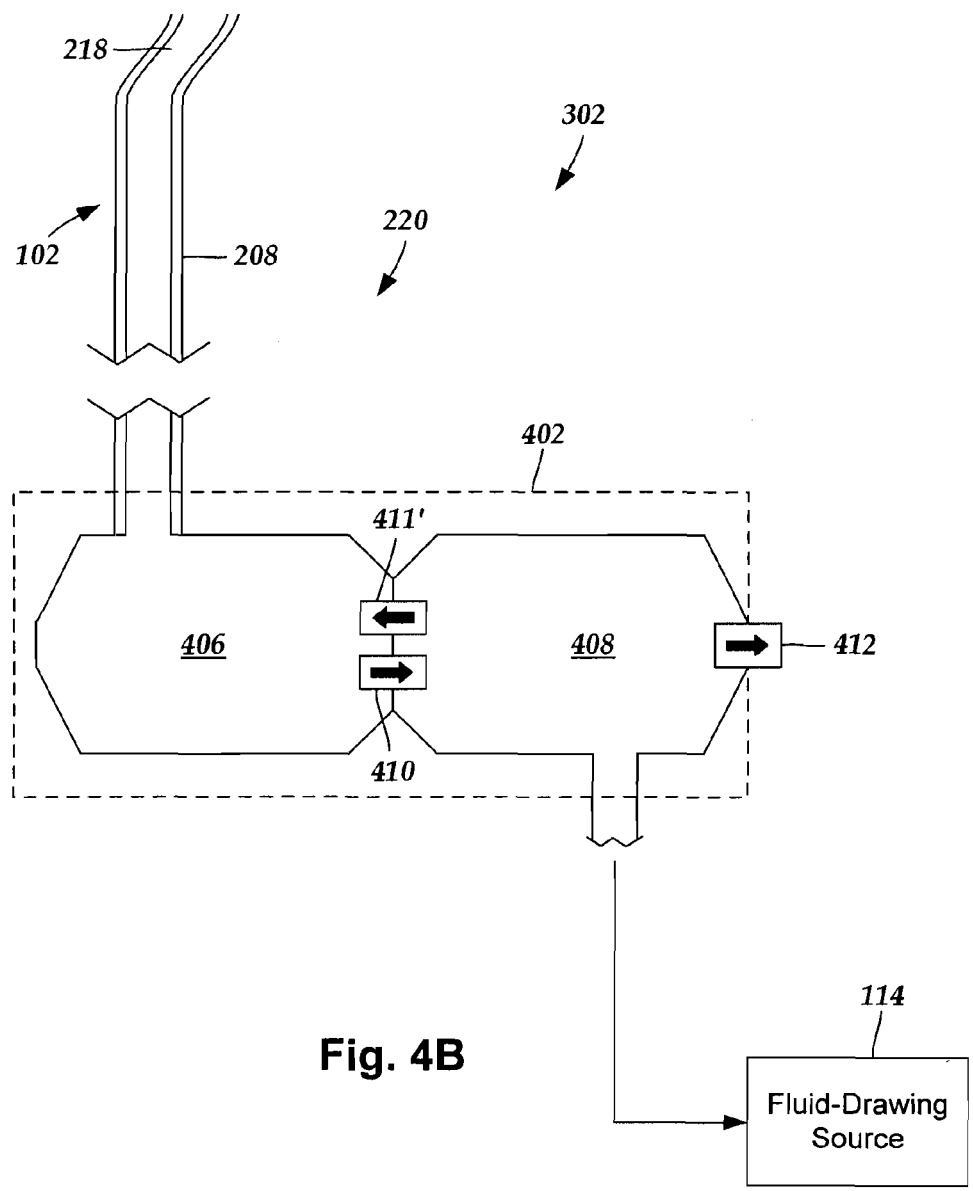
FIG. 4B is a schematic representation of another embodiment of the pressure regulation system of FIG. 3, the pressure regulation system regulating the pressure of the inter-expansion-element space relative to pressure offsets to a fluid-drawing source, according to the invention.

In at least some embodiments, the check valves 410 and 411 can be adjusted to regulate the pressure with the inter-expansion-element space 218 by comparing the pressure within the inter-expansion-element space 218 to the region 408. FIG. 4B is a schematic representation of another embodiment of the fluid pathway 220 between the inter-expansion-element space 218 and the fluid-drawing source 114. In FIG. 4B, the pressure differential of the region 406 is compared to the pressure level in the region 408 (which is at a level set by the flow rate of the fluid-drawing source 114), independent of ambient pressure (described in FIG. 4A). The check valves 410 is configured and arranged to operate as described above, with reference to FIG. 4A. The check valve 411' is configured and arranged to open into the region 406 in a manner similar to the check valve 411, described above with reference to FIG. 4A. Unlike the check valve 411, however, the check valve 411' is positioned between the regions 406 and 408. Thus, the check valve 411' compares the pressure differential of the region 406 to the region 408 (which is at a level set by the flow rate of the fluid-drawing source 114) instead of to the ambient pressure, as described in FIG. 4A.

Accordingly, the check valve 411' is configured such that under operating conditions, the check valve 411' opens when the pressure with the region 406 is at a level that meets or exceeds a threshold pressure differential below the pressure within the region 408 (i.e., the pressure obtained by the fluid-drawing source 114). Accordingly, when the check valve 411' opens, bulk movement of fluid from the region 408 occurs across the check valve 4110' and into the region 406 until the pressure differential drops to a level below the threshold pressure differential of the check valve 411' and the check valve 411' closes.

For example, in at least some embodiments, during an ablation procedure the expansion element 108 is inflated to a pressure that is no more than 2 atm (about $2 \times 10^5$ Pa). In at least some embodiments, during an ablation procedure the expansion element 108 is inflated to a pressure that is no more than 3 atm (about $3 \times 10^5$ Pa). In at least some embodiments, during an ablation procedure the expansion element 108 is inflated to a pressure that is no more than 4 atm (about $4 \times 10^5$ Pa). In at least some embodiments, during an ablation procedure the expansion element 108 is inflated to a pressure that is no more than 5 atm (about $5 \times 10^5$ Pa). In at least some embodiments, during an ablation procedure the expansion element 108 is inflated to a pressure that is no more than 6 atm (about $6 \times 10^5$ Pa). In at least some embodiments, during an ablation procedure the expansion element 108 is inflated to a pressure that is no more than 7 atm (about $7 \times 10$ Pa). In at least some embodiments, during an ablation procedure the expansion element 108 is inflated to a pressure that is no more than 8 atm (about $8 \times 10^5$ Pa). In at least some embodiments, during an ablation procedure the expansion element 108 is inflated to a pressure that is no more than 9 atm (about $9 \times 10^5$ Pa).

In at least some embodiments, during an ablation procedure the temperature of the expansion element 108 is reduced to a minimum temperature that is no greater than −20° C. In at least some embodiments, during an ablation procedure the temperature of the expansion element 108 is reduced to a minimum temperature that is no greater than −40° C. In at least some embodiments, during an ablation procedure the temperature of the expansion element 108 is reduced to a minimum temperature that is no greater than −60° C. In at least some embodiments, during an ablation procedure the temperature of the expansion element 108 is reduced to a minimum temperature that is no greater than −80° C. In at least some embodiments, during an ablation procedure the temperature of the expansion element 108 is reduced to a minimum temperature that is no greater than −100° C. In at least some embodiments, during an ablation procedure the temperature of the expansion element 108 is reduced to a minimum temperature that is no greater than −120° C.

In at least some embodiments, during an ablation procedure the temperature within the expansion element 108 is reduced from an insertion temperature to an operational temperature over a time period that is no greater than one minute. In at least some embodiments, during an ablation procedure the temperature within the expansion element is reduced from an insertion temperature to an operational temperature over a time period that is no greater than two minutes. In at least some embodiments, during an ablation procedure the temperature within the expansion element is reduced from an insertion temperature to an operational temperature over a time period that is no greater than three minutes. In at least some embodiments, during an ablation procedure the temperature within the expansion element is reduced from an insertion temperature to an operational temperature over a time period that is no greater than four minutes. In at least some embodiments, during an ablation procedure the temperature within the expansion element is reduced from an insertion temperature to an operational temperature over a time period that is no greater than five minutes.

Figure 5:
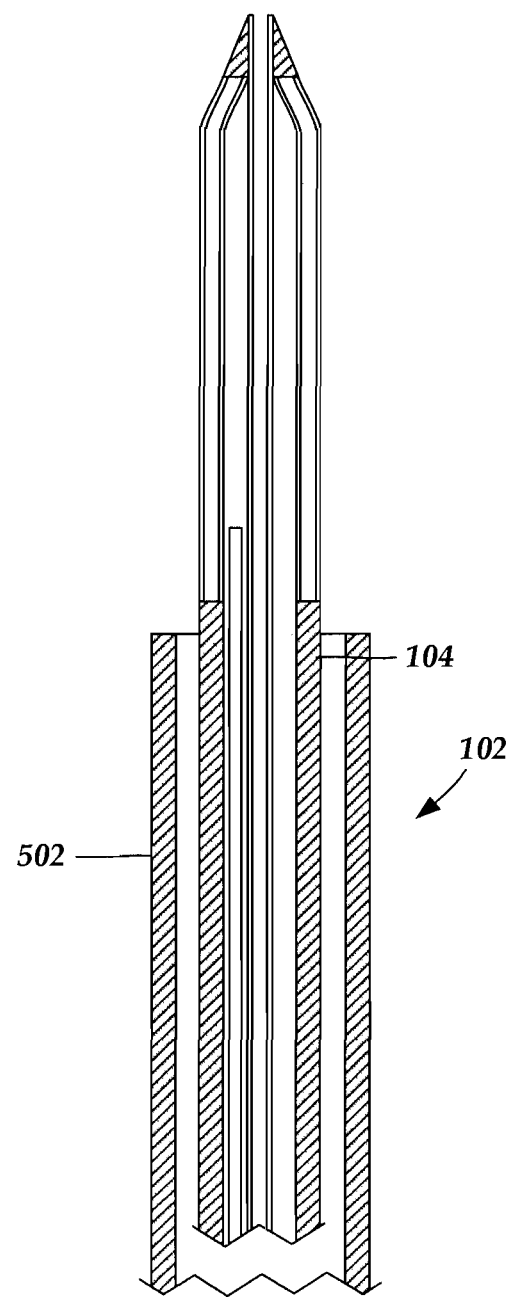
FIG. 5 is a schematic longitudinal cross-sectional view of one embodiment of a distal portion of the catheter of FIG. 2A disposed in a sheath, according to the invention.

In at least some embodiments, a sheath may be used to facilitate guidance of the catheter through patient vasculature during insertion of the catheter. FIG. 5 is a schematic longitudinal cross-sectional view of one embodiment of the distal portion 104 of the catheter 102 disposed in a sheath 502. In at least some embodiments, the sheath 502 is steerable. Once the catheter 102 is positioned at a target location, such as the ostia of the pulmonary veins in the left atrium of the heart of the patient, the sheath 502 can be removed. In at least some embodiments, the sheath may be used to maintain the positioning of the catheter 102 (e.g., at the target location). The above specification, examples and data provide a description of the manufacture and use of the composition of the invention. Since many embodiments of the invention can be made without departing from the spirit and scope of the invention, the invention also resides in the claims hereinafter appended.

What is claimed is:

1. A cryoablation catheter assembly comprising:
 a catheter having a distal portion, a proximal portion, and a longitudinal length, the catheter configured and arranged for insertion into patient vasculature, the catheter comprising a body and defining at least one coolant outtake region extending along at least a portion of the catheter;
 a guide tube at least partially disposed in the catheter;
 a coolant transfer tube at least partially disposed in the catheter, wherein the coolant transfer tube is configured and arranged to receive and transfer coolant from a coolant source to a distal end of the coolant transfer tube;
 an expansion element coupled to the distal portion of the body of the catheter, the expansion element comprising an outer layer disposed over an inner layer such that the expansion element defines an inter-expansion-element space between the inner layer and the outer layer and an intra-expansion-element space within the inner layer, the intra-expansion-element space in fluid communication with the at least one coolant outtake region and the distal end of the coolant transfer tube;

wherein the inter-expansion-element space is in fluid communication with a fluid pathway, the fluid pathway configured and arranged to transfer fluids from the inter-expansion-element space to a fluid-drawing source; and a pressure regulation system disposed along the fluid pathway, the pressure regulation system configured and arranged to passively regulate the pressure in the inter-expansion-element space using two or more check valves, wherein the pressure regulation system defines a first region and a second region fluidly separated from one another by a first check valve, and wherein a second check valve fluidly separates the first region from a region external to the catheter.

2. The cryoablation catheter assembly of claim 1, wherein the first check valve defines an opening that transitions from a closed position to an open position when a pressure differential exists between the regions that is no less than a threshold pressure differential of the first check valve.

3. The cryoablation catheter assembly of claim 1, wherein the inter-expansion-element space is defined in the first region and the fluid-drawing source is in fluid communication with the second region.

4. The cryoablation catheter assembly of claim 3, wherein the first check valve is configured and arranged to regulate the pressure within the inter-expansion-element space by comparing the pressure within the inter-expansion-element space to at least one of the pressure of a region external to the catheter or the pressure of the second region.

5. The cryoablation catheter assembly of claim 1, wherein the first check valve is configured and arranged to open when the pressure within the first region is greater than the pressure within the second region by an amount that is no less than the threshold pressure differential of the first check valve.

6. The cryoablation catheter assembly of claim 1, wherein the first check valve is configured and arranged to open when the pressure within the second region is greater than the pressure within the first region by an amount that is no less than the threshold pressure differential of the first check valve.

7. The cryoablation catheter assembly of claim 1, wherein the second check valve is configured and arranged to open when the pressure within the first region is less than the pressure of the region external to the catheter pressure by an amount that is no less than the threshold pressure differential of the second check valve.

8. The cryoablation catheter assembly of claim 1, wherein the two or more check valves additionally comprises a pressure relief valve, and wherein the pressure relief check valve fluidly separating at least one of the first region or the second region from a region external to the catheter.

9. The cryoablation catheter assembly of claim 8, wherein the pressure relief check valve is configured and arranged to open when the pressure within the fluid pathway is greater than the pressure of a region external to the catheter by an amount that is no less than the threshold pressure differential of the pressure relief check valve.

10. The cryoablation catheter assembly of claim 8, wherein the pressure relief check valve is configured and arranged to open when the pressure within the fluid pathway is at or above a critical pressure level.

11. The cryoablation catheter assembly of claim 8, wherein the threshold pressure differential of the pressure relief check valve is greater than the threshold pressure differentials of the first check valve and the second check valve.

12. The cryoablation catheter assembly of claim 1, wherein the pressure regulation system is disposed in a handle coupled to the catheter.

13. A cryoablation system comprising:
a catheter having a distal portion, a proximal portion, and a longitudinal length, the catheter configured and arranged for insertion into patient vasculature, the catheter comprising a body and defining at least one coolant outtake region extending along at least a portion of the catheter;
a guide tube at least partially disposed in the catheter;
a coolant transfer tube at least partially disposed in the catheter, wherein the coolant transfer tube is configured and arranged to receive and transfer coolant to a distal end of the coolant transfer tube;
an expansion element coupled to the distal portion of the body of the catheter, the expansion element comprising an outer layer disposed over an inner layer such that the expansion element defines an inter-expansion-element space between the inner layer and the outer layer and an intra-expansion-element space within the inner layer, the intra-expansion-element space in fluid communication with the at least one coolant outtake region and the distal end of the coolant transfer tube;
wherein the inter-expansion-element space is in fluid communication with a fluid pathway, the fluid pathway configured and arranged to transfer fluids out from the inter-expansion-element space;
a pressure regulation system disposed along the fluid pathway, the pressure regulation system configured and arranged to passively regulate the pressure in the inter-expansion-element space using two or more check valves, wherein the pressure regulation system defines a first region and a second region fluidly separated from one another by a first check valve, and wherein a second check valve fluidly separates the first region from a region external to the catheter;
a coolant source coupled to the coolant transfer tube;
a fluid-drawing source coupled to the at least one coolant outtake region and to the fluid pathway; and
a control module coupled to the catheter, the coolant source, and the fluid-drawing source, wherein the control module comprises a coolant flow controller configured and arranged for controlling the flow of coolant along the coolant transfer tube and the at least one coolant outtake region.

14. The cryoablation system of claim 13, wherein the control module further comprises at least one pressure sensor for monitoring pressure within the catheter.

15. The cryoablation system of claim 13, wherein the control module further comprises at least one temperature sensor for monitoring temperature within the catheter.

16. The cryoablation system of claim 13, wherein the coolant source comprises a coolant, the coolant being a liquefied gas under pressure.

17. A method for cryoablating patient tissue, the method comprising:
inserting a catheter in patient vasculature, the catheter having a distal portion, the catheter defining at least one coolant outtake region;
guiding the catheter in proximity to patient tissue to be ablated;
drawing coolant from a coolant source such that coolant flows along a coolant transfer tube disposed in the catheter and is sprayed into an expansion element that is disposed at the distal portion of the catheter, thereby expanding the expansion element and reducing the temperature of the expansion element to a temperature sufficiently low enough to ablate patient tissue upon contact, wherein the expansion element comprises an inner layer and an outer layer disposed over the inner layer, wherein the coolant is sprayed into an intra-expansion-element space within the inner layer, and wherein the expansion element defines an inter-expansion-element space between the inner layer and the outer layer;

contacting patient tissue with the expanded expansion element for a time period adequate to ablate tissue contacting the expansion element;

deflating the expansion element by drawing the coolant from the intra-expansion-element space along the at least one coolant outtake region and also drawing fluid from the inter-expansion-element space along a fluid pathway, wherein the coolant and the fluid are drawn by a fluid-drawing source; and passively regulating the pressure within the inter-expansion-element space using two or more check valves positioned along the fluid pathway, wherein the fluid pathway includes a pressure regulation system that defines a first region and a second region fluidly separated from one another by a first check valve, and wherein a second check valve fluidly separates the first region from a region external to the catheter.

18. The method of claim 17, wherein passively regulating the pressure within the inter-expansion-element space using two or more check valves comprises comparing the pressure within the inter-expansion-element space to at least one of the pressure of a region external to the catheter or the pressure within a region adjacent to the fluid-drawing source.

* * * * *

UNITED STATES PATENT AND TRADEMARK OFFICE
CERTIFICATE OF CORRECTION

PATENT NO. : 8,591,504 B2  
APPLICATION NO. : 12/847552  
DATED : November 26, 2013  
INVENTOR(S) : Rebecca Tin Page 1 of 1

It is certified that error appears in the above-identified patent and that said Letters Patent is hereby corrected as shown below:

In the Specification

Column 7  
Line 30: delete "refraction", and insert therefor -- retraction --.

Signed and Sealed this  
Third Day of June, 2014

Michelle K. Lee  
*Deputy Director of the United States Patent and Trademark Office*